(12) United States Patent
Hsieh et al.

(10) Patent No.: US 8,372,660 B2
(45) Date of Patent: Feb. 12, 2013

(54) QUANTITATIVE ANALYZING METHOD

(75) Inventors: Wen-Pin Hsieh, Hsinchu (TW); Yi-Jen Wu, Hsinchu (TW)

(73) Assignee: Actherm Inc, Hsinchu (TW)

( * ) Notice: Subject to any disclaimer, the term of this patent is extended or adjusted under 35 U.S.C. 154(b) by 320 days.

(21) Appl. No.: 12/366,675

(22) Filed: Feb. 6, 2009

(65) Prior Publication Data

US 2010/0092993 A1    Apr. 15, 2010

Related U.S. Application Data

(63) Continuation-in-part of application No. PCT/CN2008/001710, filed on Oct. 9, 2008.

(51) Int. Cl.
*G01N 33/544* (2006.01)

(52) U.S. Cl. ........ 436/530; 436/501; 436/518; 436/528; 436/529; 436/164; 436/169; 436/170; 435/283.1; 435/287.1; 435/287.2; 435/287.7; 422/50; 422/400; 422/401; 422/420

(58) Field of Classification Search .................. 436/501, 436/518, 528, 529, 530, 164, 169, 170; 435/283.1, 435/287.1, 287.2, 287.7; 422/50, 400, 401, 422/420
See application file for complete search history.

(56) References Cited

U.S. PATENT DOCUMENTS

| | | | |
|---|---|---|---|
| 4,483,714 A * | 11/1984 | Yamaue et al. ............ | 106/279 |
| 4,774,192 A * | 9/1988 | Terminiello et al. ......... | 436/530 |
| 4,828,801 A | 5/1989 | Lombardy wife Alric et al. | |
| 5,821,073 A * | 10/1998 | Lee ............................. | 435/7.92 |
| 6,210,907 B1 | 4/2001 | Cha | |
| 6,670,115 B1 | 12/2003 | Zhang | |
| 6,756,019 B1 | 6/2004 | Dubrow et al. | |
| 7,455,816 B2 | 11/2008 | Steuer et al. | |
| 7,785,865 B2 * | 8/2010 | Qinwei ....................... | 435/287.8 |
| 2005/0142666 A1 * | 6/2005 | Audeh et al. ................. | 436/523 |
| 2006/0141469 A1 * | 6/2006 | Rossier et al. .................... | 435/6 |
| 2006/0188395 A1 | 8/2006 | Taniike et al. | |
| 2007/0089987 A1 * | 4/2007 | Neel et al. ................ | 204/403.01 |
| 2008/0019866 A1 | 1/2008 | Paek et al. | |
| 2008/0108096 A1 | 5/2008 | Ralph | |
| 2009/0104690 A1 * | 4/2009 | Bayliff et al. .............. | 435/287.1 |

FOREIGN PATENT DOCUMENTS

| | | |
|---|---|---|
| CN | 1139982 A | 1/1997 |
| CN | 1146557 A | 4/1997 |
| CN | 1309294 A | 8/2001 |

(Continued)

OTHER PUBLICATIONS

U.S. Appl. No. 12/307,274, filed Jan. 1, 2009, Hsieh, Wen-Pin, et. al.

(Continued)

*Primary Examiner* — Melanie Y Brown
(74) *Attorney, Agent, or Firm* — Ming Chow; Sinorica, LLC

(57) ABSTRACT

This invention discloses an analyzing method for detecting a specific analyte in a fluid sample. The method comprises the following steps. First, a substrate is provided. The substrate has a channel provided concavely on an upper surface thereof. The channel comprises a first area, a second area and a third area, and these three areas are connected sequentially. Each of the second and the third areas comprises a nitrocellulose layers containing a reaction material and formed at the bottom thereof. The nitrocellulose layer of the third area can absorb a fixed volume of the fluid sample. Second, the fluid sample is applied to the first area and delivered by the second area and then to the third area. Finally, the reaction material reacts with the specific analyte in the fluid sample to produce a signal for detection.

11 Claims, 3 Drawing Sheets

FOREIGN PATENT DOCUMENTS

| | | | |
|---|---|---|---|
| CN | 1334924 | A | 2/2002 |
| CN | 1407339 | A | 4/2003 |
| CN | 1429337 | A | 7/2003 |
| CN | 1519563 | A | 8/2004 |
| CN | 1830390 | A | 9/2006 |
| CN | 1851459 | A | 10/2006 |
| CN | 1854728 | A | 11/2006 |
| CN | 1954214 | A | 4/2007 |
| CN | 101303358 | A | 11/2008 |
| JP | 2007139649 | A | 6/2007 |
| TW | 97135411 | | 9/2008 |
| TW | 97135929 | | 9/2008 |
| TW | 97137420 | | 9/2008 |
| TW | 97216918 | | 9/2008 |
| TW | 97217136 | | 9/2008 |
| TW | 97139296 | | 10/2008 |
| TW | 97139824 | | 10/2008 |
| TW | 97139825 | | 10/2008 |
| TW | 97218077 | | 10/2008 |
| TW | M350706 | | 2/2009 |
| TW | M354070 | | 4/2009 |
| TW | M359693 | | 6/2009 |
| WO | WO9008322 | A1 | 7/1990 |
| WO | WO0042434 | A1 | 7/2000 |
| WO | WO0184153 | A1 | 11/2001 |
| WO | WO2004086042 | A1 | 10/2004 |
| WO | WO2006047869 | A1 | 5/2006 |
| WO | WO2007081330 | A1 | 7/2007 |
| WO | WO2007128286 | A1 | 11/2007 |
| WO | PCT-CN2008001531 | | 8/2008 |
| WO | PCT-CN2008001551 | | 8/2008 |
| WO | PCT-CN2008001613 | | 9/2008 |
| WO | PCT-CN2008001710 | | 10/2008 |
| WO | PCT-CN2008001747 | | 10/2008 |
| WO | PCT-CN2008001750 | | 10/2008 |

OTHER PUBLICATIONS

U.S. Appl. No. 12/306,972, filed Dec. 30, 2008, Hsieh, Chih-Wei et. al.

* cited by examiner

QUANTITATIVE ANALYZING METHOD

This application is a continuation in part of PCT/CN2008/001710 filed on Oct. 9, 2008.

BACKGROUND OF THE INVENTION

1. Technical Field

The present invention relates to a quantitative analyzing method of a fluid sample, and more particularly, to a quantitative analyzing method of a fluid sample for the biochemical assay and immunological assay.

2. Description of Related Art

Conventional analytical strips used in biochemical or immunological assays usually have a substrate or a baseboard provided with a channel or a microfluidic channel. While such channel is typically bordered by a non-absorptive material, and the viscosity of the fluid sample to be analyzed is usually high for the sample is mainly composed of proteins or carbohydrates, part of the fluid sample tends to adhere to the surface of the channel and will not be reacted. Such scenario, if happens, will not only disadvantageously cause the waste of the fluid sample to be analyzed, but also will adversely affects the accuracy of quantifying assays.

In addition, the conventional analytical strip may facilitate the flow of the fluid sample by microfluidic channels so that the fluid sample will be delivered via the capillary force exerted by the structures of such channels to the reaction area. Another alternative approach to deliver the fluid sample involves applying a driving force, such as by a pressurizing means, at the time the fluid sample is introduced into the channel so that the fluid sample is propelled to the reaction area through the channel. However, either one of the aforementioned approaches tends to cause air bubbles occurring after the fluid sample is introduced into the channel. These bubbles, either large or small, will block the channel and result in inaccurate analyzing results.

Furthermore, the manufacturing process of the channels or microfluidic channels on the current substrates is usually involves molding, injection forming or imprinting, using expensive die making process such as micro-machining or LIGA (abbreviation of "Lithographie GalVanoformung Abformung", or "Lithography Electroforming Micro Molding" in english) which, coupled with early wear and tear of molds, increases the total cost incurred in making analytical strips.

BRIEF SUMMARY OF THE INVENTION

In order to overcome the abovementioned shortcomings, the present invention provides a quantitative analyzing method for detecting a specific analyte in a fluid sample. The method comprises the steps of:

(1) providing a substrate having an upper surface concavely formed with at least one channel. The channel comprises a first area, a second area and a third area, and these three areas are connected sequentially. Each of the second and third areas has a nitrocellulose layer formed at the bottoms thereof. Both the nitrocellulose layers have a hollow-matrix conformation. The second area is configured for delivering the fluid sample and the third area is configured for where the fluid sample reacts. The nitrocellulose layer of the second area comprises an average thickness that is not greater than the average thickness of the nitrocellulose layer of the third area. The nitrocellulose layer of the third area is capable of absorbing a fixed volume of the fluid sample. In addition, a reaction material is formed in the hollow-matrix conformation of the nitrocellulose layers;

(2) applying the fluid sample to the first area of the substrate, so that the fluid sample is delivered by the second area and then to the third area;

(3) absorbing the fixed volume of the fluid sample by the nitrocellulose layer of the third area; and (4) allowing the reaction material in the third area and the specific analyte in the fluid sample to react and produce a signal.

Hence, a primary object of the present invention is to provide a quantitative analyzing method for detecting a specific analyte in a fluid sample, wherein the method comprises providing a substrate formed with a channel having absorbent nitrocellulose layers. Since the nitrocellulose has a constant volumetric absorptive capacity and thus allows a quantitative assay to be conducted via controlling the volume of the nitrocellulose layers.

Another object of the present invention is to provide a quantitative analyzing method for detecting a specific analyte in a fluid sample, wherein the method comprises providing a substrate formed with a channel having nitrocellulose layers of hollow-matrix conformations, which is capable of destroying the air bubbles in the fluid sample when the fluid sample flows through the hollow matrix, as well as preventing the bubbles from blocking the channel or the microfluidic channel of the substrate. Thus, an accurate result of the quantitative assay could be assured.

Still another object of the present invention is to provide a quantitative analyzing method for detecting a specific analyte in a fluid sample that has the step of providing substrates with thin absorptive nitrocellulose layers on the bottom of channel. The thin absorptive nitrocellulose layers act as sample delivering and/or separating function. The channel thus has lower residual of samples in contrast to the traditional microfluidic channel, and low volume of samples needed for multi-analytes detection in a test is realized.

BRIEF DESCRIPTION OF THE SEVERAL VIEWS OF THE DRAWINGS

The invention as well as a preferred mode of use, further objects and advantages thereof will be best understood by referring to the following detailed description of an illustrative embodiment in conjunction with the accompanying drawings, wherein.

DETAILED DESCRIPTION OF THE INVENTION

The present invention discloses a quantitative analyzing method for detecting a specific analyte in a fluid sample in which the physical and chemical principles as well as solution application techniques involved are well known to those skilled in the art. Therefore, a detailed description of such principles and techniques is omitted herein for brevity. Besides, the drawings referred to in the following description are not drawn to actual scale and need not be so because they are intended to demonstrate features of the present invention only schematically.

Figure 1:
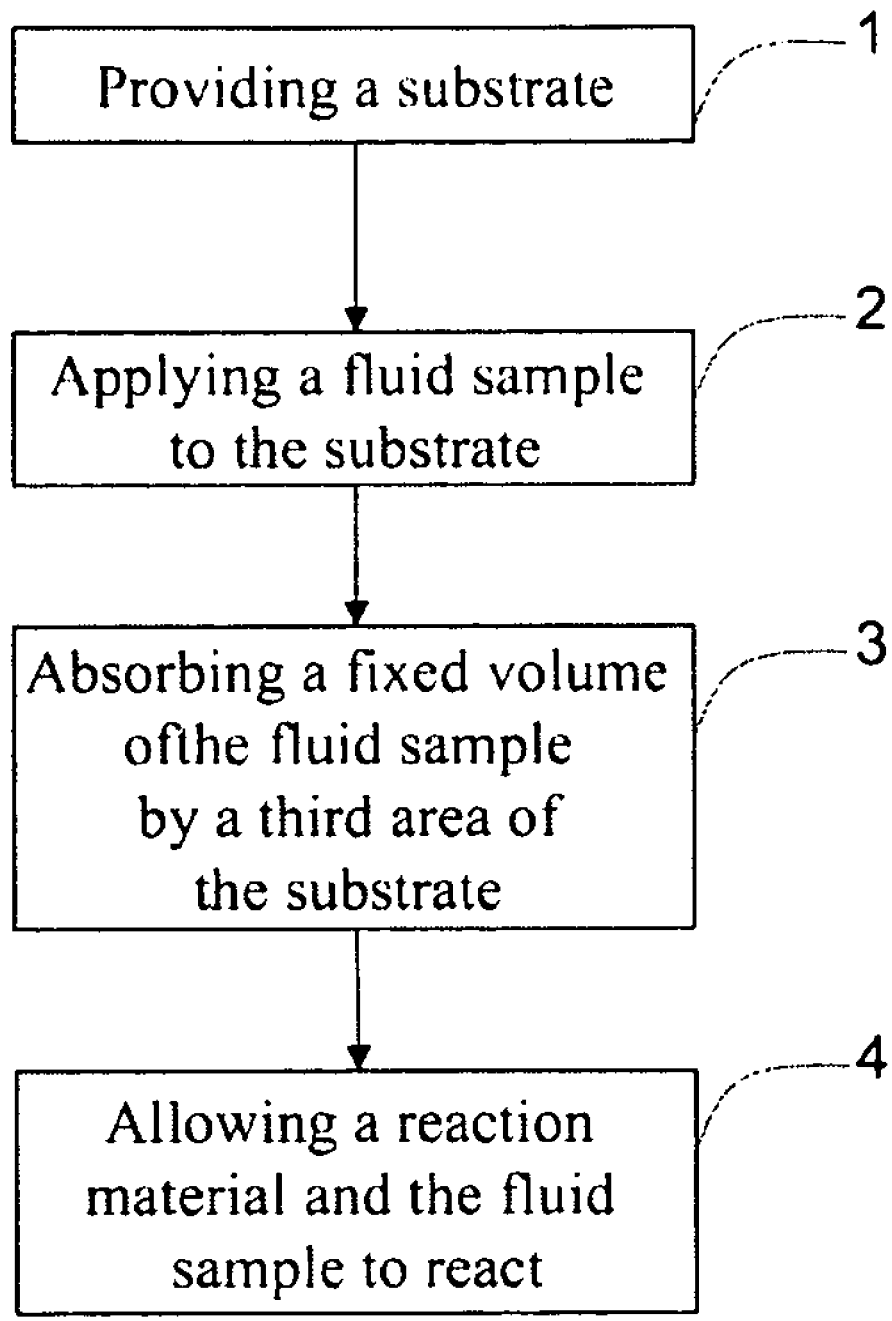
FIG. 1 is a flowchart of a quantitative analyzing method for detecting a specific analyte in a fluid sample according to a preferred embodiment of the present invention.

Referring to FIG. 1, according to a preferred embodiment of the present invention, a quantitative analyzing method for detecting a specific analyte in the fluid sample comprises the following steps.

Figure 2:
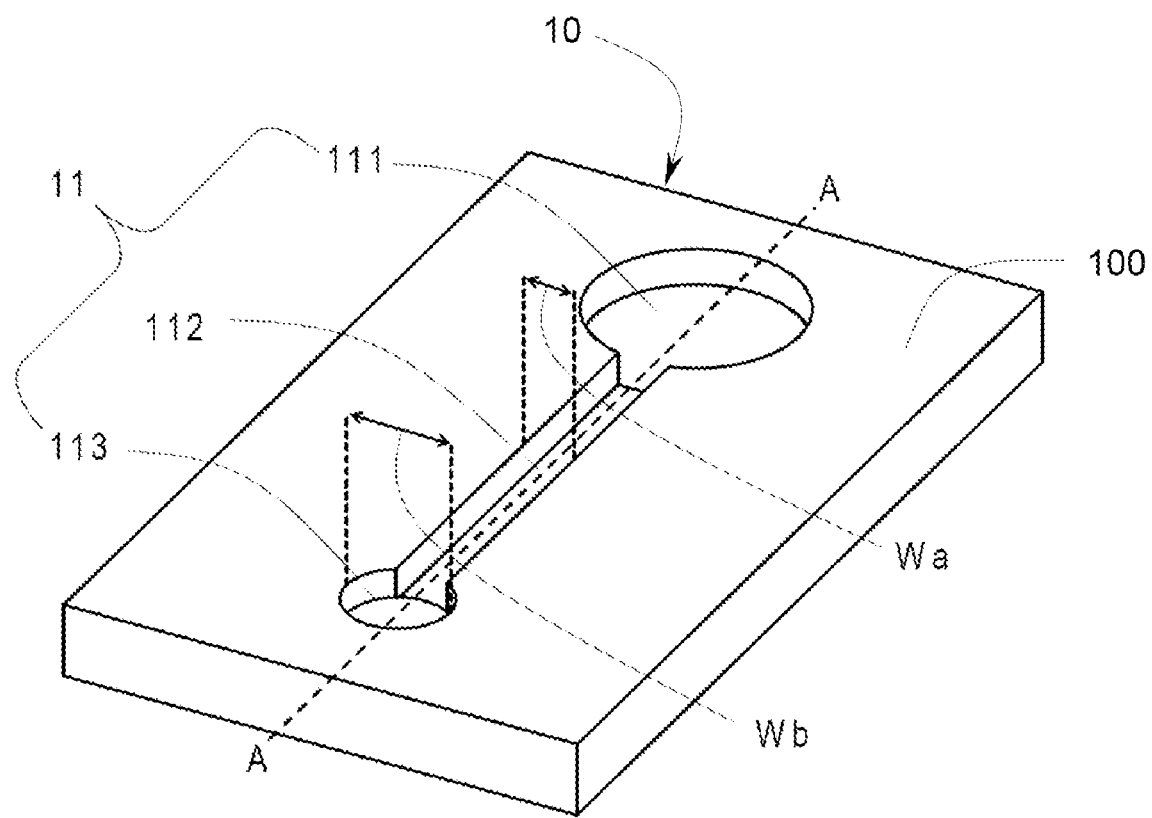
FIG. 2 is a schematic perspective view of a substrate provided in the quantitative analyzing method for detecting a specific analyte in a fluid sample according to the preferred embodiment of the present invention.
Figure 3:
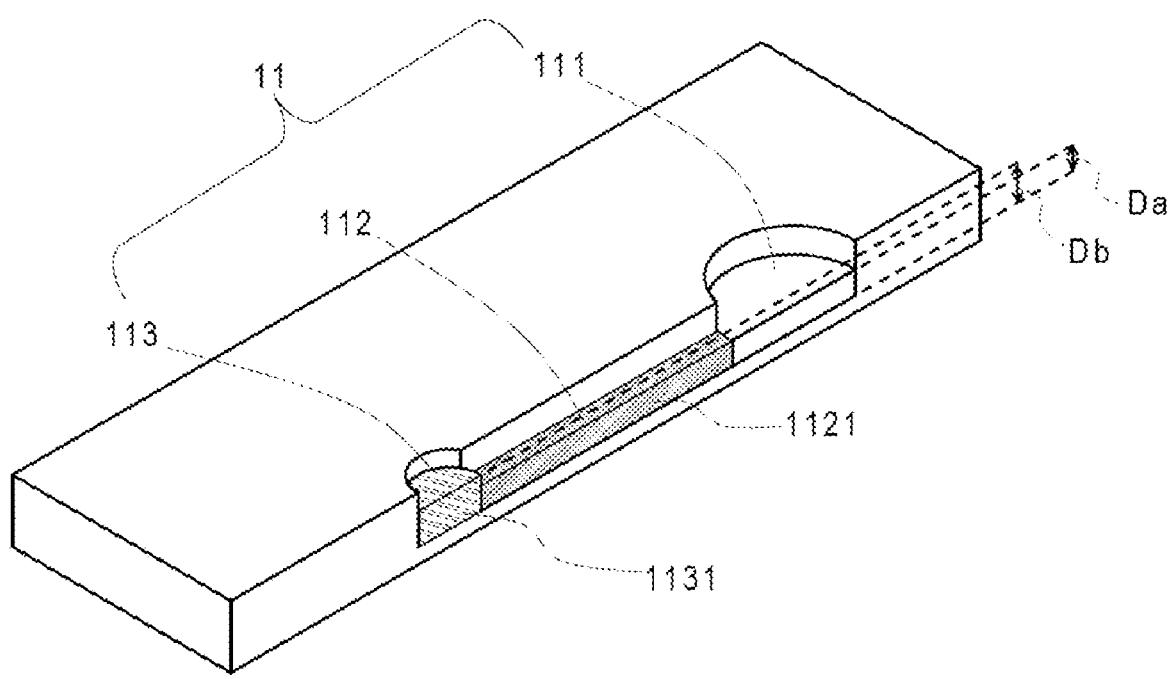
FIG. 3 is a schematic sectional view of the substrate provided in quantitative analyzing method for detecting a specific analyte in a fluid sample according to the preferred embodiment of the present invention.

At step 1, a substrate 10 is provided. Referring to FIG. 2, the substrate 10 has an upper surface 100 concavely provided with at least one channel 11. The channel 11 includes a first area 111, a second area 112 and a third area 113. These three areas 111, 112, and 113 are connected sequentially. The substrate 10 is preferably made of a biocompatible material. Please refer now to FIG. 3, which is a sectional view of the substrate 10 taken along a line A-A in FIG. 2. Nitrocellulose layers 1121 and 1131, each having a hollow-matrix conformation, are formed at bottoms of the second and third areas 112 and 113, respectively. The second area 112 is configured for delivering a fluid sample and the third area 113 is where the fluid sample reacts. The nitrocellulose layer 1121 has an average thickness Da that is not greater than the average thickness Db of the nitrocellulose layer 1131. Because nitrocellulose has a constant volumetric absorptive capacity, the nitrocellulose layer 1131 can absorb a constant volume of the fluid sample. Furthermore, the hollow-matrix conformation of the nitrocellulose layers 1121 and 1131 contain a reaction material whose composition varies from the categories of analytes in the fluid sample to be detected.

At step 2, a fluid sample is applied to the first area 111 of the substrate 10, so that the fluid sample is delivered by the second area 112 and then to the third area 113.

At step 3, the nitrocellulose layer 1131 of the third area 113 absorbs the fixed volume of the fluid sample.

At step 4, the reaction material in the third area 113 reacts with the specific analyte in the fluid sample to produce a signal for detection. The signal can be a luminescent signal, a fluorescent signal, a photoabsorptive signal or an electric signal.

In addition, in order to reduce the influence of capillary effect exerted between the channels and the fluid sample, the configurations of the channel 11 disclosed in the present invention is not similar to that of the conventional microchannel. Preferably, a width Wa of the second area 112 and a width Wb of the third area 113 are both at least 0.3 mm.

The nitrocellulose layers 1121 and 1131 are formed in the following manner. To begin with, a nitrocellulose powder is mixed with an organic solvent containing esters and ketones to form a nitrocellulose solution. Then the nitrocellulose solution is poured onto the bottoms of the second and third areas 112 and 113 in a casting process. After drying, the nitrocellulose layer 1121 is formed at the bottom of the second area 112 and the nitrocellulose layer 1131 is formed at the bottom of the third area 113. For a better result of the casting process, the channel 11 preferably has a surface roughness ranging from 3 μm to 50 μm.

In order to obtain a hollow matrix with a better structure, the nitrocellulose power is mixed with the organic solvent containing esters and ketones preferably at a volumetric ratio of 1:9. Because nitrocellulose has a constant volumetric absorptive capacity, the required volume of the nitrocellulose solution can be derived from the desired volume of the fluid sample to be adsorbed and analyzed before casting. As a result, the required volume of the fluid sample of the analytical strip 1 will be fixedly set, so that the resultant analytical strip 1 is suitable for an assay in a small volume.

The reaction materials in the nitrocellulose layers 1121 and 1131 can be formed by the two following manners that one is to be formed in a readily formed nitrocellulose layers and the other is to be formed simultaneously with the nitrocellulose layers.

The reaction materials are formed in a readily formed nitrocellulose layers in the following manners. A reaction solution containing the reaction material is injected into the nitrocellulose layers 1121 and 1131 which have already been readily formed. The reaction solution is then dried by air-drying process or lyophilization so that the reaction material is left in the nitrocellulose layers 1121 and 1131 in the form of powder.

However, in an alternative approach, to form the reaction materials simultaneously with the nitrocellulose layers, the reaction solution containing the reaction material is firstly mixed with the nitrocellulose solution comprising the nitrocellulose powder and the organic solvent containing esters and ketones, before the resultant mixture is casting onto the bottoms of the second and third areas 112 and 113, so that after drying by air-drying or lyophilization, the nitrocellulose solution is dried to form the nitrocellulose layers 1121 and 1131 while the reaction material is left therein in a powder form.

The quantitative analyzing method of the present invention can be applied to either biochemical assays or immunological assay. As the analytes to be detected vary, different assays are required, and different assays produce different signals. For example, a biochemical assay may use enzyme to catalyze reaction between analytes in the fluid sample to be detected and a chemical reagent so as to produce a specific signal for detection. Therefore, in order to perform the biochemical assay, the reaction material contains a suitable enzyme and the corresponding chemical reagent. On the other hand, if it is desired to detect the presence of a certain protein, such as α-fetoprotein, in a specimen, it will be necessary to use an antibody with specificity for the targeted protein and the corresponding chemical reagent suitable for recognition of the antibody to the targeted protein, thereby producing a signal for detection. Consequently, to perform the immunological detection, the reaction material contains such immunological reagents as antibodies and corresponding chemical reagents. Thus, the substrate 10 provided in the present invention is applicable to detection of various compounds in a variety of biological specimens, such as urine, blood and other fluid specimens.

The preferred embodiment of the present invention described above utilizes a substrate formed with a channel having three areas. However, the quantitative analyzing method according to the present invention may also be implemented with a substrate formed with a channel having a fourth area (not shown) for accommodating excess of the fluid sample in the channel, in addition to and arranged sequentially after the first, second and third areas. The fourth area is also provided with a nitrocellulose layer containing a reaction material, and the conformation and the forming method of the nitrocellulose layer, ingredients and the preferred volumetric ratio of the nitrocellulose solution forming the nitrocellulose layer, and the composition of the reaction material are all similar to those disclosed in the foregoing preferred embodiment and will not be repeated herein.

The above description is intended only to demonstrate the preferred embodiment of the present invention and not to limit the scope of the invention. Moreover, as the contents disclosed herein should be readily understood and can be implemented by those skilled in the art, all equivalent changes or modifications which do not depart from the spirit of the present invention should be encompassed by the appended claims.

The invention claimed is:

1. A quantitative analyzing method for detecting a specific analyte in a fluid sample, comprising steps of:

providing a substrate having an upper surface concavely provided with at least one channel including a first area, a second area and a third area which are connected sequentially, the second and third areas having bottoms thereof formed respectively with thin absorptive nitrocellulose layers each having a hollow-matrix conformation, and the nitrocellulose layers at the bottoms of the second area and the third area being formed by pouring a nitrocellulose solution onto the bottoms of the second and third areas in a casting process that is followed by a drying process, wherein the channel has a surface roughness ranging from 3 μm to 50 μm, the nitrocellulose solution being formed by mixing a nitrocellulose powder with a solvent containing esters and ketones at a volumetric ratio of 1:9, the second area being configured for delivering the fluid sample and the third area being where the fluid sample reacts, each of the second and third areas having a width of at least 0.3 mm, the nitrocellulose layer of the second area comprising an average thickness which is smaller than that of the nitrocellulose layer of the third area, and the nitrocellulose layer of the third area being capable of absorbing a constant volume of the fluid sample; and wherein a reaction material is formed in the hollow-matrix conformation of the nitrocellulose layer of the third area;

applying the fluid sample to the first area, so that the fluid sample is delivered by the second area and then to the third area;

absorbing the fixed volume of the fluid sample by the nitrocellulose layer of the third area; and allowing the reaction material in the third area and the specific analyte in the fluid sample to react and produce a signal.

2. The quantitative analyzing method as claimed in claim 1, wherein the substrate is made of a biocompatible material.

3. The quantitative analyzing method as claimed in claim 1, wherein the reaction material is in a powder form and formed in the hollow-matrix conformation of the nitrocellulose layers by injecting a reaction solution containing the reaction material into the nitrocellulose layers followed by a drying process.

4. The quantitative analyzing method as claimed in claim 3, wherein the drying process is selected from the group consisting of a lyophilization process and an air-drying process.

5. The quantitative analyzing method as claimed in claim 1, wherein the reaction material is in a powder form and formed in the hollow matrices of the nitrocellulose layers by mixing a reaction solution containing the reaction material with the nitrocellulose solution followed by a drying process so that the nitrocellulose solution forms the nitrocellulose layers while the reaction material is left in the nitrocellulose layers in the powder form.

6. The quantitative analyzing method as claimed in claim 5, wherein the drying process is selected from the group consisting of a lyophilization process and an air-drying process.

7. The quantitative analyzing method as claimed in claim 1, wherein the reaction material comprises an enzyme and a chemical reagent.

8. The quantitative analyzing method as claimed in claim 1, wherein the reaction material comprises an antibody and a chemical reagent.

9. The quantitative analyzing method as claimed in claim 1, wherein the signal is selected from the group consisting of a luminescent signal, a fluorescent signal and a photoabsorptive signal.

10. The quantitative analyzing method as claimed in claim 1, wherein the signal is an electric signal.

11. The quantitative analyzing method as claimed in claim 1, wherein the signal is selected from the group consisting of a luminescent signal, a fluorescent signal and a photoabsorptive signal.

* * * * *